US010416686B2

(12) United States Patent
Shoham et al.

(10) Patent No.: US 10,416,686 B2
(45) Date of Patent: Sep. 17, 2019

(54) COMPACT APPARATUS FOR CONTINUOUS PRODUCTION OF A PRODUCT SUBSTANCE FROM A STARTER MATERIAL GROWN IN AQUACULTURE CONDITIONS

(71) Applicant: GreenOnyx LTD, Ganey Tikva (IL)

(72) Inventors: Tsipi Shoham, Ganey Tikva (IL); Benjamin Shoham, Ganey Tikva (IL)

(73) Assignee: GreenOnyx LTD, Tel Aviv (IL)

( * ) Notice: Subject to any disclaimer, the term of this patent is extended or adjusted under 35 U.S.C. 154(b) by 736 days.

(21) Appl. No.: 14/408,949

(22) PCT Filed: Jun. 18, 2013

(86) PCT No.: PCT/US2013/046346
§ 371 (c)(1),
(2) Date: Dec. 17, 2014

(87) PCT Pub. No.: WO2013/192195
PCT Pub. Date: Dec. 27, 2013

(65) Prior Publication Data
US 2015/0234394 A1    Aug. 20, 2015

Related U.S. Application Data

(60) Provisional application No. 61/660,814, filed on Jun. 18, 2012.

(51) Int. Cl.
*G05D 7/06* (2006.01)
*A01G 33/00* (2006.01)
(Continued)

(52) U.S. Cl.
CPC ............ *G05D 7/0635* (2013.01); *A01G 2/00* (2018.02); *A01G 33/00* (2013.01); *A01H 4/001* (2013.01);
(Continued)

(58) Field of Classification Search
None
See application file for complete search history.

(56) References Cited

U.S. PATENT DOCUMENTS 4,146,993 A    4/1979  Freeman, Sr.
4,441,145 A    4/1984  Antkowiak
(Continued)

FOREIGN PATENT DOCUMENTS

AU    2009213072 A1    4/2010
CN       100430468 C    11/2008
(Continued)

OTHER PUBLICATIONS

Extended European Search Report issued in European Patent Appln. No. 13806582.6, dated Jan. 18, 2016.
(Continued)

*Primary Examiner* — Jason Lin
(74) *Attorney, Agent, or Firm* — Sterne, Kessler, Goldstein & Fox P.L.L.C.

(57) ABSTRACT

An apparatus for continuous growth and production of a product substance. The apparatus may comprise an input unit for receiving at least one starting material, wherein the starting material is one of at least an aquatic organism; a growing unit for continuous aquatic growth of the at least one starting material to produce at least a culture; a buffering unit for accumulating and upholding at least a portion of the culture grown in the growing unit, wherein the buffering unit is configured to balance between demand and supply of a product substance produced by the apparatus; a nozzle for delivery of a demanded fraction of the upheld portion of the culture as the product substance; and a control unit connected to the input unit, the growing unit, the buffering unit and configured to control the operation of the apparatus.

27 Claims, 6 Drawing Sheets

(51) Int. Cl.
*A01H 4/00* (2006.01)
*C12M 1/00* (2006.01)
*C12M 1/34* (2006.01)
*C12M 1/36* (2006.01)
*A01G 2/00* (2018.01)
*G05B 15/02* (2006.01)

(52) U.S. Cl.
CPC ............ *C12M 21/02* (2013.01); *C12M 29/06* (2013.01); *C12M 41/32* (2013.01); *C12M 41/34* (2013.01); *C12M 41/36* (2013.01); *C12M 41/46* (2013.01); *C12M 41/48* (2013.01); *G05B 15/02* (2013.01)

(56) References Cited

U.S. PATENT DOCUMENTS

| | | | |
|---|---|---|---|
| 5,197,263 A | 3/1993 | Midtling et al. | |
| 5,269,819 A | 12/1993 | Porath | |
| 5,353,745 A * | 10/1994 | Fahs, II | A01K 63/003 119/226 |
| 5,744,041 A * | 4/1998 | Grove | C02F 3/30 210/602 |
| 5,993,030 A | 11/1999 | Barcel | |
| 6,192,833 B1 | 2/2001 | Brune et al. | |
| 6,458,398 B1 * | 10/2002 | Smith | A23B 4/16 426/320 |
| 6,561,134 B1 * | 5/2003 | Mikami | A23K 10/22 119/204 |
| 6,905,838 B1 | 6/2005 | Bittner | |
| 7,094,562 B2 | 8/2006 | Bittner | |
| 7,176,024 B2 | 2/2007 | Branson et al. | |
| 7,287,488 B2 | 10/2007 | Taylor et al. | |
| 7,415,144 B2 | 8/2008 | Imaizumi et al. | |
| 7,499,573 B2 | 3/2009 | Tanabata et al. | |
| 7,531,350 B2 | 5/2009 | Shiau | |
| 7,582,415 B2 | 9/2009 | Straus | |
| 7,643,134 B2 | 1/2010 | Berndt | |
| 7,690,330 B2 | 4/2010 | Miller | |
| 7,824,904 B1 | 11/2010 | Dimanshteyn | |
| 7,997,025 B1 | 8/2011 | Masse | |
| 8,022,373 B2 | 9/2011 | Maiya | |
| 8,043,496 B1 * | 10/2011 | Schuh | B01D 17/0211 210/121 |
| 8,064,661 B2 | 11/2011 | Komori et al. | |
| 8,159,675 B2 | 4/2012 | Kiyota | |
| 8,175,327 B2 | 5/2012 | Beaty et al. | |
| 8,245,440 B2 | 8/2012 | Ryan et al. | |
| 8,523,385 B2 | 9/2013 | Lu et al. | |
| 8,569,050 B1 * | 10/2013 | Ericsson | C12N 1/12 435/292.1 |
| 8,713,850 B2 | 5/2014 | Seebo | |
| 8,800,202 B2 | 8/2014 | Rusiniak | |
| 8,993,314 B2 | 3/2015 | Eckelberry et al. | |
| 9,021,739 B2 | 5/2015 | Koo et al. | |
| 2001/0016788 A1 * | 8/2001 | Hauwiller | A01B 79/005 700/283 |
| 2005/0034676 A1 | 2/2005 | Taylor et al. | |
| 2005/0074146 A1 | 4/2005 | Jones et al. | |
| 2005/0180608 A1 | 8/2005 | Tanabata et al. | |
| 2006/0102851 A1 | 5/2006 | Jalink et al. | |
| 2006/0143731 A1 | 6/2006 | Timmis et al. | |
| 2006/0240544 A1 | 10/2006 | Shiau | |
| 2007/0092962 A1 | 4/2007 | Sheppard | |
| 2007/0094926 A1 | 5/2007 | Branson et al. | |
| 2007/0151522 A1 | 7/2007 | Brauman | |
| 2008/0173249 A1 | 7/2008 | Miller | |
| 2009/0113790 A1 | 5/2009 | Erd | |
| 2009/0291485 A1 | 11/2009 | Shigematsu et al. | |
| 2010/0005711 A1 | 1/2010 | McNeff | |
| 2010/0028977 A1 | 2/2010 | Ng et al. | |
| 2010/0108146 A1 * | 5/2010 | Ferreira | A61L 2/07 137/1 |
| 2010/0162621 A1 | 7/2010 | Seebo | |
| 2011/0045564 A1 * | 2/2011 | Dhamwichukorn | C12N 1/06 435/170 |
| 2011/0051414 A1 | 3/2011 | Bailey et al. | |
| 2011/0116688 A1 | 5/2011 | Li et al. | |
| 2011/0153053 A1 * | 6/2011 | Kim | A01G 9/246 700/103 |
| 2011/0216953 A1 | 9/2011 | Callahan et al. | |
| 2011/0290202 A1 | 12/2011 | Smith et al. | |
| 2012/0003728 A1 | 1/2012 | Lanoue et al. | |
| 2012/0043907 A1 | 2/2012 | Lu et al. | |
| 2012/0149091 A1 | 6/2012 | Wilkerson et al. | |
| 2012/0282677 A1 | 11/2012 | Brod et al. | |
| 2012/0309081 A1 * | 12/2012 | Herzog | C12M 21/02 435/288.7 |
| 2013/0038727 A1 | 2/2013 | Clark | |
| 2013/0045531 A1 | 2/2013 | Weaver et al. | |
| 2013/0283683 A1 | 10/2013 | Ringbom et al. | |
| 2014/0234896 A1 | 8/2014 | McHugh | |
| 2014/0268635 A1 | 9/2014 | Aikala et al. | |
| 2015/0089867 A1 | 4/2015 | Abbott et al. | |

FOREIGN PATENT DOCUMENTS

| | | |
|---|---|---|
| CN | 101909429 A | 12/2010 |
| CN | 102439129 A | 5/2012 |
| JP | 1120230 A | 5/1989 |
| JP | 8228602 A | 9/1996 |
| JP | 2005056657 A | 3/2005 |
| JP | 2008283937 A | 11/2008 |
| JP | 2010267591 A | 11/2010 |
| JP | 2011120557 A | 6/2011 |
| WO | 9407361 | 4/1994 |
| WO | 03017749 A1 | 3/2003 |
| WO | 2005070121 A2 | 8/2005 |
| WO | 2006042371 A1 | 4/2006 |
| WO | 2009142765 A2 | 11/2009 |
| WO | 2010115655 A1 | 10/2010 |
| WO | 2010123943 A1 | 10/2010 |
| WO | 2013192195 A1 | 12/2013 |
| WO | 2014006233 A1 | 1/2014 |

OTHER PUBLICATIONS

Office Action issued in Chinese Patent Appln. No. 201380038670.6, dated Dec. 21 2015.
International Preliminary Report on Patentability issued in International Appl. No. PCT/US2013/046346, dated Dec. 23, 2014.
Written Opinion of the International Searching Authority issued in International Appl. No. PCT/US2013/046346, dated Sep. 25, 2013.
International Search Report issued in International Appl. No. PCT/US2013/046346, dated Sep. 25, 2013.
Owen Fletcher, The Future of Agriculture May Be Up, The Wall Street Journal, Oct. 15, 2012, <http://online.wsj.com/article/SB10000872396390443855804577602960672985508.html>, 7 pages.
Vertical Farming Technology <http://www.terraspheresystems.com>, accessed Apr. 21, 2015.
Martha Irvine, In a Chicago suburb, an indoor farm goes 'mega', <http://bigstory.ap.org/article/chicago-suburb-indoor-farm-goes-mega>, Mar. 28, 2013, 8 pages.
Microfarms and bioreactors in modular systems, <http://www.algaeindustrymagazine.com/scalable-algae-microfarms-part-5/>, Jan. 6, 2013, 10 pages.
J.P. Bitog et al., Application of computational fluid dynamics for modeling and designing photobioreactors for microalgae production: A review, Computers and Electronics in Agriculture, vol. 76, Issue 2, May 2011, pp. 131-147.
Francesca L. Crowe et al., Risk of hospitalization or death from ischemic heart disease among British vegetarians and nonvegetarians: results from the EPIC-Oxford cohort study, AM J Clin Nutr, vol. 97, No. 3, Mar. 2013, pp. 597-603.
M. Dominique Ashen, Vegetarian Diets in Cardiovascular Prevention; Curr Treat Options Cardiovas Med., vol. 15, Issue 6, Aug. 9, 2013, pp. 735-745.
Tao Huang et al., Cardiovascular Disease Mortality and Cancer Incidence in Vegetarians: A Meta-Analysis and Systemic Review, Ann Nutr Metab, vol. 60, No. 4, Jun. 2012, pp. 233-240.

(56) References Cited

OTHER PUBLICATIONS

ScienceDaily, "Vegetarianism can reduce risk of heart disease by up to a third", <http://www.ox.ac.uk/media/news_stories/2013/130130.html>, Jan. 30, 2013, 2 pages.

Claire T. McEvoy et al., Vegetarian diets, low-meat diets and health: a review: Cambridge Journals—Public Health Nutrition, vol. 15, Issue 12, Dec. 2012, pp. 2287-2294.

Invitation to Pay Additional Fees and, Where Applicable, Protest Fee issued in International Appl. No. PCT/IB2015/000398, dated Jul. 3, 2015.

Xue Chen et al., "Lumostatic Strategy for Microalgae Cultivation Utilizing Image Analysis and Chlorophyll Content as Design Parameters, Bioreource Technology," vol. 102, No. 10, Feb. 15, 2011, pp. 6005-6012.

Ivo Havlik et al., "Monitoring of Microalgal Cultivations with On-line, Flow-Through Microscopy," Algal Research, vol. 2, No. 3, Apr. 26, 2013, pp. 253-257.

Kanhaiya Kumar et al., "Use of Image Analysis Tool for the Development of Light Distribution Pattern Inside the Photobioreactor for the Algal Cultivation," Bioreseouce Technology, vol. 143, Jun. 3, 2013, pp. 88-95.

J.M. Sandnes et al., "Real-time Monitoring and Automatic Density Control of Large-Scale Microalgal Cultures Using Near Infrared (NIR) Optical Density Sensors, Journal of Biotechnology," vol. 122, No. 2, Mar. 23, 2006, pp. 209-215.

Miguel V. Córdoba-Matson et al., "Evaluation of Isochrysis Galbana (clone T-ISO) Cell Numbers by Digital Image Analysis of Color Intensity," Journal of Applied Phycology, vol. 22, No. 4, Sep. 19, 2009, pp. 427-434.

Arne Bluma et al., "In-situ Imaging Sensors for Bioprocess Monitoring: State of the Art," Analytical and Bioanalytical Chemistry, vol. 398, No. 6, Sep. 12, 2010, pp. 2429-2438.

Ivo Havlik et al., "Online Monitoring of Large Cultivations of Microalgae and Cyanobacteria," Trends in Biotechnology, vol. 31, No. 7, May 23, 2013, pp. 406-414.

\* cited by examiner

COMPACT APPARATUS FOR CONTINUOUS PRODUCTION OF A PRODUCT SUBSTANCE FROM A STARTER MATERIAL GROWN IN AQUACULTURE CONDITIONS

CROSS REFERENCE TO RELATED APPLICATIONS

This application claims the benefit of U.S. provisional application No. 61/660,814 filed on Jun. 18, 2012, the contents of which are herein incorporated by reference.

TECHNICAL FIELD

This invention generally relates to a compact system for production of substances and more particularly to a compact system for producing substances from organic substances.

BACKGROUND

By 2050 the world's population is estimated to reach 9.1 billion, 34 percent higher than that of today. Urbanization is also predicted to continue at an accelerated pace, and about 70 percent of the world's population will have become urbanized. In order to feed this larger, more urban population, food production must increase proportionately. Yet, increasing production is not sufficient alone to achieve food security. It must be complemented by enhancing nutritional quality and food safety, while ensuring environmental sustainability, urban accessibility and affordability.

The global rise of chronic non-infectious and degenerative diseases, such as cardiovascular diseases, type II diabetes, asthma, cancer, dementias, hypertension, osteoporosis, attention deficit disorder, and attention deficit hyperactivity disorder (ADD/ADHD), are directly linked to our nutrition deficient food and diet habits, which result from our busy modern lifestyle and to the high consumption of low nutritional quality processed food. Unfortunately, the desired nutrition dense diet, based on natural non-industrialized fresh food, is with only limited access, and will become more and more difficult to provide year round at the required quantities and at affordable prices, in order to meet the ever-increasing demand.

It would be therefore advantageous to produce and deliver a customized highly-nutritional fresh foodstuff, supplied year-round at significant yearly quantities directly to the consumer on site and per demand, safely and at assured affordable costs. It would be further advantageous to provide additional substances other than edible substances.

SUMMARY

Certain embodiments disclosed herein include an apparatus for continuous growth, production, and deliver of a product substance. The apparatus comprises at least one input unit for receiving at least one starting material, wherein the starting material is one of at least an aquatic organism; at least one growing unit for continuous aquatic growth of the at least one starting material to produce at least a culture; at least one buffering unit for accumulating and upholding at least a portion of the culture grown in the at least one growing unit, wherein the buffering unit is configured to continually balance between demand and supply of a product substance produced by the apparatus and to enable to provide a customized product substance; at least one nozzle for delivery of a demanded fraction of the upheld portion of the culture as the product substance; and a control unit connected to the at least one input unit, the at least one growing unit, the at least one buffering unit, and the at least one nozzle, wherein the control unit is configured to control the operation of the apparatus to ensure that the grown culture meets predefined environmental conditions, ensure safety of the product substance, and ensure that the supply of the product substance is per demand.

Certain embodiments disclosed herein also include a method for continuously growing and producing a product substance. The method comprises receiving at least one starting material wherein the starting material is one of at least an aquatic organism by at least one input unit; operating at least one growing unit for continuously growing of the at least one starting material to produce at least a culture; operating at least one buffering unit for accumulating and upholding at least a portion of the culture grown in the at least one growing unit, wherein operating the at least one buffering unit further includes balancing between demand and supply of a product substance produced by the apparatus; operating one or more nozzles for delivering at least a demanded fraction of the accumulated upheld culture as the product substance; and operating a control unit connected to the at least one input unit, the at least one growing unit, the at least one buffering unit, and the at least one nozzle, wherein the control unit is configured to ensure that the grown culture meets optimal environmental conditions.

BRIEF DESCRIPTION OF THE DRAWINGS

The subject matter disclosed is particularly pointed out and distinctly claimed in the claims at the conclusion of the specification. The foregoing and other objects, features, and advantages of the invention will be apparent from the following detailed description taken in conjunction with the accompanying drawings.

DETAILED DESCRIPTION

Figure 1:
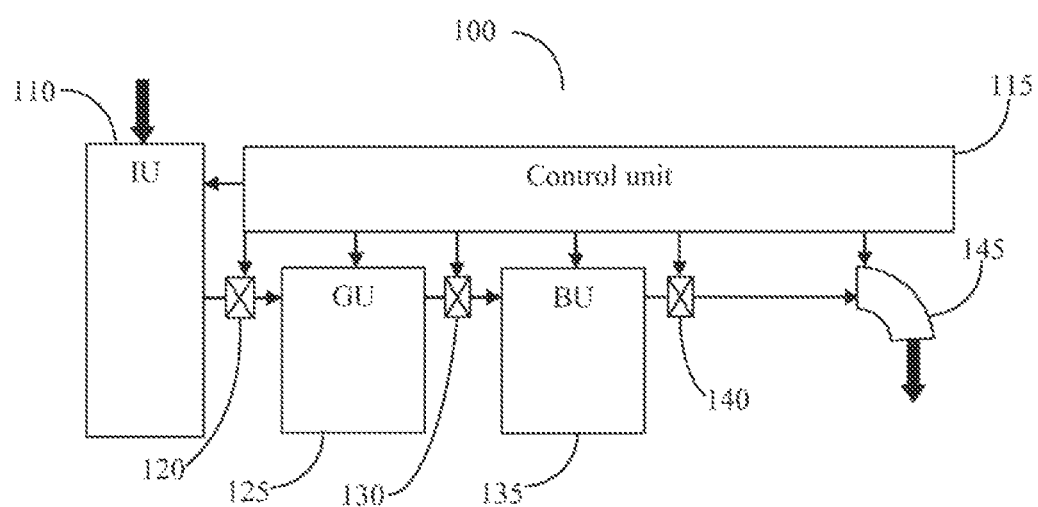
FIG. 1 is a schematic diagram of the system constructed according to one embodiment.

It is important to note that the embodiments disclosed by the invention are only examples of the many advantageous uses of the innovative teachings herein. In general, statements made in the specification of the present application do not necessarily limit any of the various claimed inventions. Moreover, some statements may apply to some inventive features but not to others. In general, unless otherwise indicated, singular elements may be in plural and vice versa with no loss of generality. In the drawings, like numerals refer to like parts through several views.

According to certain embodiments the disclosed system produces one or more product substances, for example, foodstuff or cosmetic substances, from aquatic organisms culture. The system is enabled to customize a product substance at the consumer's premise according to specific needs and preferences. The system comprises an input stage, a growing stage, an accumulation and upholding stage, and an output stage, operated automatically by a control unit. In one embodiment, the control unit may comprise a user interface by which the control unit receives instructions and settings from a user. The input stage is configured to receive consumables, such as an aquatic organism starter material, liquids, fertilizers, and sensing components. A sensing component may be, for example, a pH colorimetric detector to detect elevated $CO_2$ in correlation to contamination. In the growing stage, the aquatic organism is allowed to grow by providing and controlling the input of the consumables as well as other environmental parameters, such as, substrate flow, air, moisture, light, potential hydrogen and temperature. In the harvest accumulation and upholding stage, the aquatic organism viability and wellbeing is supported until a request for an output is received. In the output stage, a fraction of the accumulated and upheld harvest, which is a portion of the culture, developed from the starter material, is processed into a product substance. At the output stage, additional adjustment may be allowed according to specific customer needs, requirements and preferences.

FIG. 1 is an exemplary and non-limiting schematic diagram of a system 100 constructed according to one embodiment. The system 100 comprises five compartments, an input unit (IU) 110, a growing unit (GU) 125, a buffering unit (BU) 135, and a nozzle 145 for the delivery of a fraction of the culture of the aquatic organism to be used as foodstuff or a cosmetic substance. It should be noted that although not illustrated in FIG. 1, the system 100 may include a plurality of GUs 125, BUs 135, and nozzles 145.

The units 110, 125, 135 and 145 are typically subsystems, each comprised of one or more compartments (not shown in FIG. 1), and the operation of each of the units is performed under the control of the control unit 115. The control unit 115 further controls a series of valves 120, 130 and 140 that allow the delivery of content from one compartment to the other. In one embodiment, one or more of the valves are unidirectional allowing the delivery of content from a first unit to a second unit, for example, from the IU 110 to the GU 125, or in the other direction from the GU 125 to the IU 110. In another embodiment, one or more of the valves are bidirectional allowing the delivery of content from a first unit to a second unit and from the second unit to the first unit, e.g., allowing flow from unit 110 to 125 as well as from unit 125 to unit 110, the direction controlled by the control unit 115. In one embodiment, one or more of the valves in the system 100 are constructed without any moving parts.

An aquatic organism is used as a starter material and inserted into the IU 110. Edible aquatic organism starter material can be, for example, but not by way of limitation, a plant from the Lemnaceae family (Duckweed), especially, from the *Spirodela, Landoltia, Lemna, Wolffiella* and *Wolffia* genera, edible micro-algae and macro-algae. In another embodiment, the starter material of aquatic organisms, which are not necessarily edible, are used.

The IU 110 is configured to receive the starter material as different organism developmental states and forms. For example, but not by way of limitation, the starter material may be received as a pre-matured or matured plant, as an attenuated form, a dormant form, an etiolated form, and/or as seeds. A predefined volume of starter material is input to the system every predefined time interval. In the IU 110, the starter material enters via a safe condition procedure, and is then fertilized and exposed to light in a controlled and monitored way, stimulating maturation to cultivation state. The monitoring and control of the fertilizing process is enabled by the control unit 115.

The control unit monitors and controls the input starter material growth and maturation in the IU 110, the quality of the input starter material, the transition of the matured culture to GU 125 and the culture growth in the GU 125, and then the harvest cycle. The harvest cycle includes the control of at least the timing, frequency and size of culture fraction to be relocated from the GU 125 to the BU 135, the slow growth in BU 135, the output preparation treatments and the transition to the nozzles as further described herein below.

The control unit 115 performs physiological, chemical and physical measurements that relate to one or more of the organism's viability state, growth rate, growth cycle, and culture safety conditions, as well as environmental growth conditions. In one embodiment, the measurements achieved by one or more sensors (not shown) are operated by the control unit 115. Such sensors may be, for example, but not limited to, a temperature sensor, a pressure sensor, a light intensity meter, a potential hydrogen sensor, an electrical conductivity sensor, a sound sensor, an ultrasound sensor, a moistness sensor, an image sensor (or camera), and the like.

In a preferred embodiment, the culture images taken under different lighting conditions, are analyzed to provide indications of, the growth rate, safety, and state of the organism, and thus allows the control unit 115 to execute necessary steps in order to assure optimal growth conditions. The environmental growth conditions include, for example, temperature in the system 100, ion concentration, $O_2$ and $CO_2$ concentrations, light intensity, and so on.

In another embodiment, culture images captured by the image sensor can be correlated with one or more measurements provided by the sensors listed above. The correlation of the information allows for monitoring of the growth rate/conditions of the organism. It should be noted that the correlation of images with addition sensory information allows the utilization of standard sensors that does not require complex calibration and adaptation processes, therefore reducing the complexity and cost of the system 100.

The aquatic organism is then transferred through the valve 120 to the GU 125 that enables the growth of the material by providing and maintaining (bio-mimicking) the specific organism species' optimal native environmental conditions. The control unit 115 continues monitoring and adjusting these growth conditions in the GU 125 to meet culture volume and quality specifications as may be predetermined by a user, or a third party expert.

Optimal native environmental conditions are defined in the culture volume and quality specifications and are provided as at least one of physical conditions, chemical conditions, and physiological conditions. The physical conditions typically include light, and temperature level and cycle, water and air flow rate and cycle, air pressure and moisture level, and organism dynamic concentrations. The chemical conditions used to grow the substrate typically include potential hydrogen, ion concentration, growth solution turbidity and optical density, fertilizer compounds, dissolved $CO_2$ and $O_2$, and air composition. The physiological conditions typically include organism morphological patterns, size, and color tones and patterns.

The aquatic organism is then transferred through a valve 130 to the BU 135. The BU 135 accumulates and upholds the aquatic organism until a request for an output substance is received. That is, the BU 135 allows the balance between the demand and supply of the consumable (output) substance. In an embodiment, operation of the valve 130 can be viewed as harvesting of a fraction of the aquatic organism culture. That is, the valve 130 under the control of the control unit 115, fraction of aquatic organism culture flows through the valve 130 to the BU 135. Upon receiving a request for output substance, under the control of the control unit 115, a portion of a culture of the aquatic organism is treated, to meet output criteria, such as food grade criteria, and is then transferred through a valve 140 and supplied as foodstuff or a cosmetic substance to the user through the nozzle 145. The treatment process may include washing the culture biomass fraction with clean water and other substances that can be used for this purpose.

The monitoring and control of the whole harvest process (valve 130 to nozzle 145) is performed by the control unit 115. The continuous operation of the system 100 enables the continuous delivery of output material in optimal conditions of freshness. Such delivery is achieved because prior to the output delivery, the organism is kept viable in slow-growth pre-delivery conditions in the BU 135 under the monitoring of the control unit 115. In one embodiment, the delivery process may include the collection of the conditioned growth medium or substrate from one of: the GU 125 or the BU 135, which includes components secreted from the organism, in combination or without the organism itself.

The control unit 115 is also configured to control the supply in order to meet the demand of the consumed foodstuff. That is, in a case of a low demand the growing conditions are set their sub-optimal mode, such as reducing light intensity, such that the aquatic growth pace is low. On the other hand, when an increase in the demanded is detected, the growing conditions are set to provide higher pace of aquatic growth. As the system 100 is a self-contained closed system, the aquatic growth and the harvesting is performed independently of the topoclimate or microclimate conditions that exist where the system 100 is placed.

Figure 2:
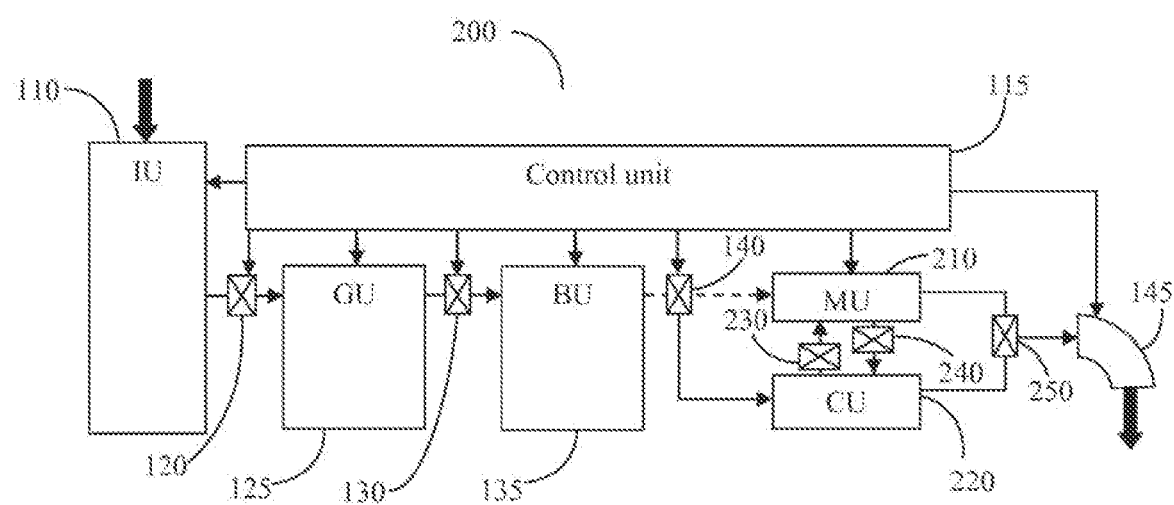
FIG. 2 is a schematic diagram of the system constructed according to another embodiment.

FIG. 2 is an exemplary and non-limiting schematic diagram of a system 200 constructed according to another embodiment. The system 200 includes similar units IU 110, GU 125, BU 135, control unit 115, nozzles 145, and valves 120, 130, and 140 as discussed with reference to FIG. 1 above. In the system 200, prior to output delivery, a portion of the accumulated and upheld culture is transferred from the BU 135 through the valve 140 to a modification unit (MU) 210 or to a customization unit (CU) 220, or both, in parallel or in a bidirectional sequential order (i.e., CU 220 to the MU 210 through the valve 230 or MU 210 to CU 220 through the valve 240). The transfer of a portion of the accumulated and upheld culture to the MU and/or CU in parallel or a bidirectional sequential order is performed under the control of the control unit 115 (FIG. 2, dashed arrow).

The MU 210 operation can be performed in one or more compartments. The operation of the MU 210 is performed under the control of the control unit 115. The MU 210 enables altering of the output foodstuff or cosmetic substance in terms of the ingredients' content. This can be applied by a change in selected growth conditions factors, or a combination of changes in different factors performed by the CU 220 that may cause or induce such modification. These factors may include, for example, light intensity level and/or spectrum, substrate or air temperature, air gas mix, fertilizer mix changes, and any combination of these or other factors at different time intervals and lengths. In one embodiment, the modification may comprise purification and concentration of bioactive components from the organism and/or the conditioned growth medium or substrate. The modified requested portion of the accumulated culture is then transferred through a valve 250 and supplied as foodstuff or a cosmetic substance to the user through the one or more nozzles 145. According to one embodiment, the operation of the MU 210 may be controlled by the BU 135.

The CU 220 operation can be integrated into one unit or performed with separate subsystems or any combinations as desired and can be comprised from one or more compartments. The operating of the CU 220 is performed under the control of the control unit 115. In the CU 220, the requested portion of the accumulated culture of the aquatic organism can be treated as a fresh output following a clean step with no additional processing or can go through one or more physical changes according to the user preferences, such as but not limited to, grounding and/or squeezing fresh foodstuff to a form of a raw liquid paste product, drying to a pre-defined level ranging from 95%-5% water, turning into a concentrated paste at a desired viscosity level, or grinding into a powder.

These changes may include various flavoring reagents and procedures or ingredient add-ons to reach a required outcome for further use or consumption. The demanded fraction of the upheld culture of the aquatic organism is then transferred through a valve 250 and supplied as foodstuff or a cosmetic substance to the user through the one or more nozzles 145. In another embodiment, the demanded fraction of the upheld culture of the aquatic organism can be transferred through both the MU 210 and the CU 220, and then through valve 250, and then supplied as foodstuff or a cosmetic substance to the user through the one or more nozzles 145.

It should be understood that the use of a plurality of parallel units in each of the stages of the system 200 allows for the creation of multiple different foodstuffs or cosmetic products and allows for the mixture of different productions of foodstuff and cosmetic substances. For example, if there are two compartments in the IU 110, it is possible to provide starter materials of two different organisms that may be grown separately, in two separate compartments in the GU 125 and then mixed into a single foodstuff. While the BU 135 may be comprised of a plurality of compartments therein, the control unit 115 may control the production so that the content of the compartments in the GU 125 are transferred into separate compartments of the BU 135.

Figure 3:
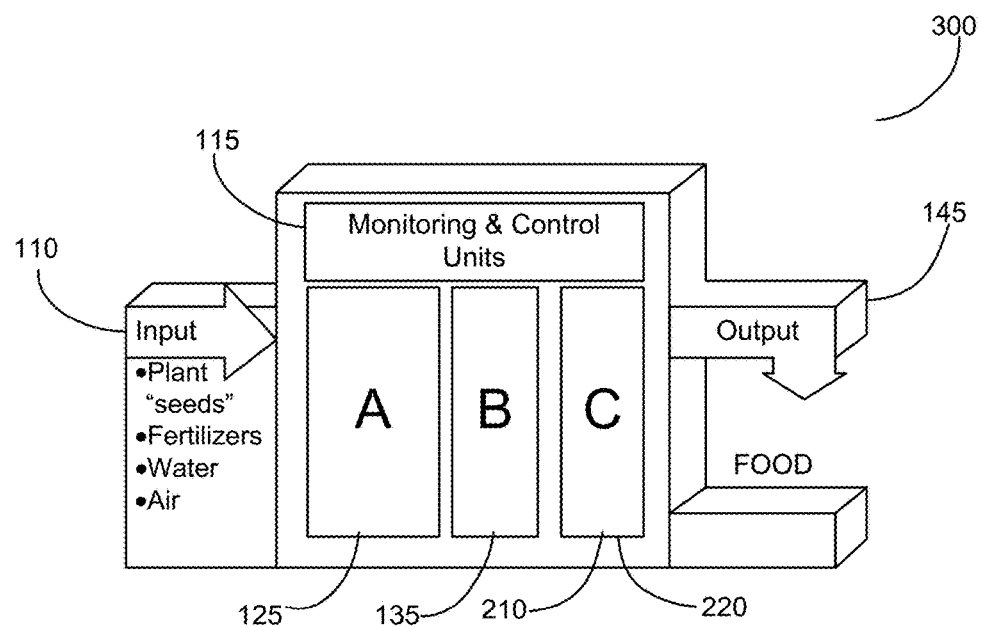
FIG. 3 is a layout drawing of the system according to an embodiment.

FIG. 3 is an exemplary and non-limiting layout drawing of a system 300 according to an embodiment. The system comprises six compartments, the IU 110, the GU 125 (A), the BU 135 (B), the MU 210 and CU 220 (C) and one or more nozzles 145 for the delivery of the harvested fraction and the demanded portion of the upheld culture of the aquatic organism to be used as foodstuff or a cosmetic substance. It should be noted that even though the operation of the delivery of the aquatic organism through the system 300 is made horizontally, each unit of the system 300 may be of a different height allowing substance to flow in a vertical direction.

Figure 4:
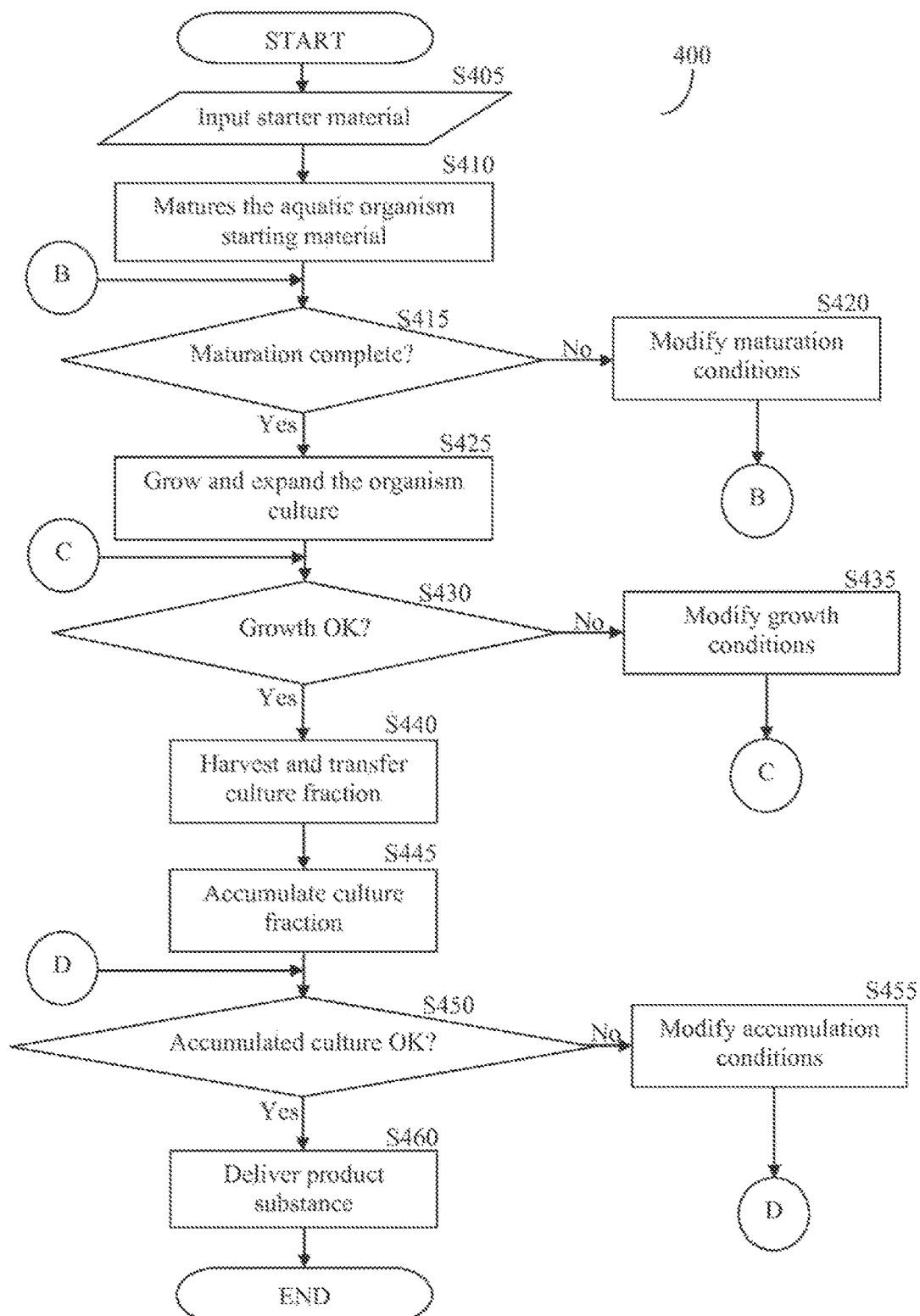
FIG. 4 is a flowchart describing the operation of growing the aquatic organism according to one embodiment.

FIG. 4 shows an exemplary and non-limiting flowchart 400 describing the operation of growing the aquatic organism according to one embodiment. In S405 the aquatic organism starter material is inserted into the system through the IU 110, where it is prepared to enter the GU 125. At this stage the user is able to select different materials (plant species) using the same system or mixing species to meet different nutritional or functional needs.

In S410, the aquatic organism matures through the IU 110. The nature of the growth is discussed in greater detail hereinabove with respect to FIGS. 1 and 2. In S415, it is checked whether the maturation of the starter culture of the aquatic organism is satisfactory, based on an array of standard physiological, chemical, and/or physical measurements that can be digitally read by the control unit 115, and if so, execution continues with S425; otherwise, execution continues with S420.

In S420, the maturation process is modified and controlled by the control unit 115, then and execution returns to S415. In S425, the matured aquatic organism culture is further grown and expanded. The nature of the growth is discussed in greater detail hereinabove with respect to FIGS. 1 and 2. During the growth process (S425), the control unit 115 is configured to control any one or more of the following conditions: types of fertilizers, temperature range and cycle, vapor pressure and humidity, potential hydrogen (pH), electrical conductivity (EC), carbon dioxide ($CO_2$) concentration, oxygen concentration ($O_2$), light, substrate transparency, water, air, culture density, organism morphology, organism mass density and biochemical features, and precipitate. Therefore, the organism culture grows and expands continuously under the monitoring and control of the control unit 115.

In S430, it is checked whether the growing culture meets an array of predefined physiological, chemical and physical criteria that are measured and controlled by the control unit 115 as further described hereinabove with respect to FIG. 1 and if so, execution continues with S440; otherwise, execution continues with S435. In S435, one or more of the growth conditions are modified and controlled by the control unit 115 and execution returns to S430. In S440, a culture fraction is harvested as further discussed hereinabove with respect to FIG. 1 and FIG. 3. In S445 the culture fraction is accumulated and upheld by the BU 135 as further discussed hereinabove with respect to FIG. 1 to FIG. 3.

In S450, it is checked whether the accumulated and upheld culture meets an array of defined physiological, chemical and/or physical criteria that are measured and controlled by the control unit 115 as further described hereinabove with respect to FIG. 1. If so, execution continues with S460; otherwise, execution continues with S455. In S455, one or more of the accumulation conditions are modified and controlled by the control unit 115, and then execution returns to S450. In S460, the product substance is delivered as further discussed hereinabove with respect to FIG. 1 and FIG. 3.

Figure 5A:
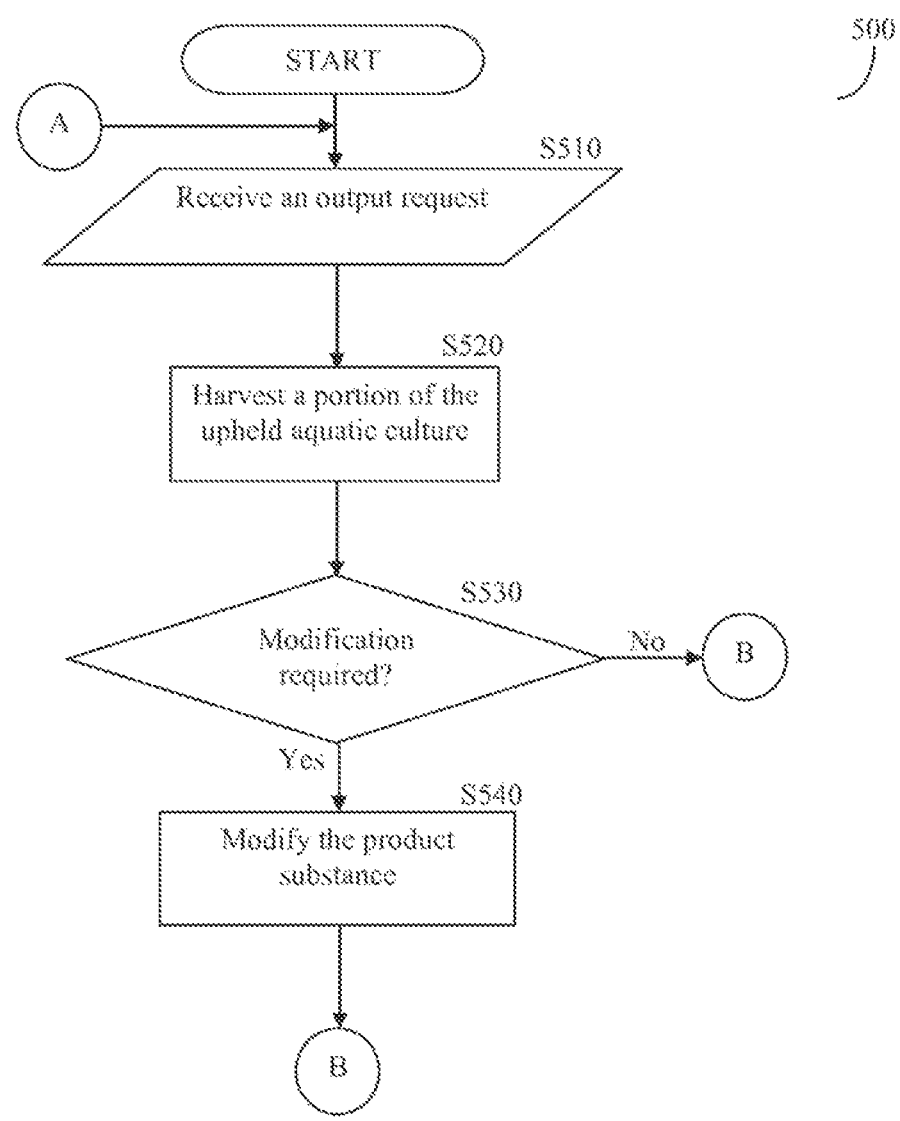
FIG. 5 is a flowchart describing the operation of delivering an output of a consumable substance according to one embodiment.
Figure 5B:
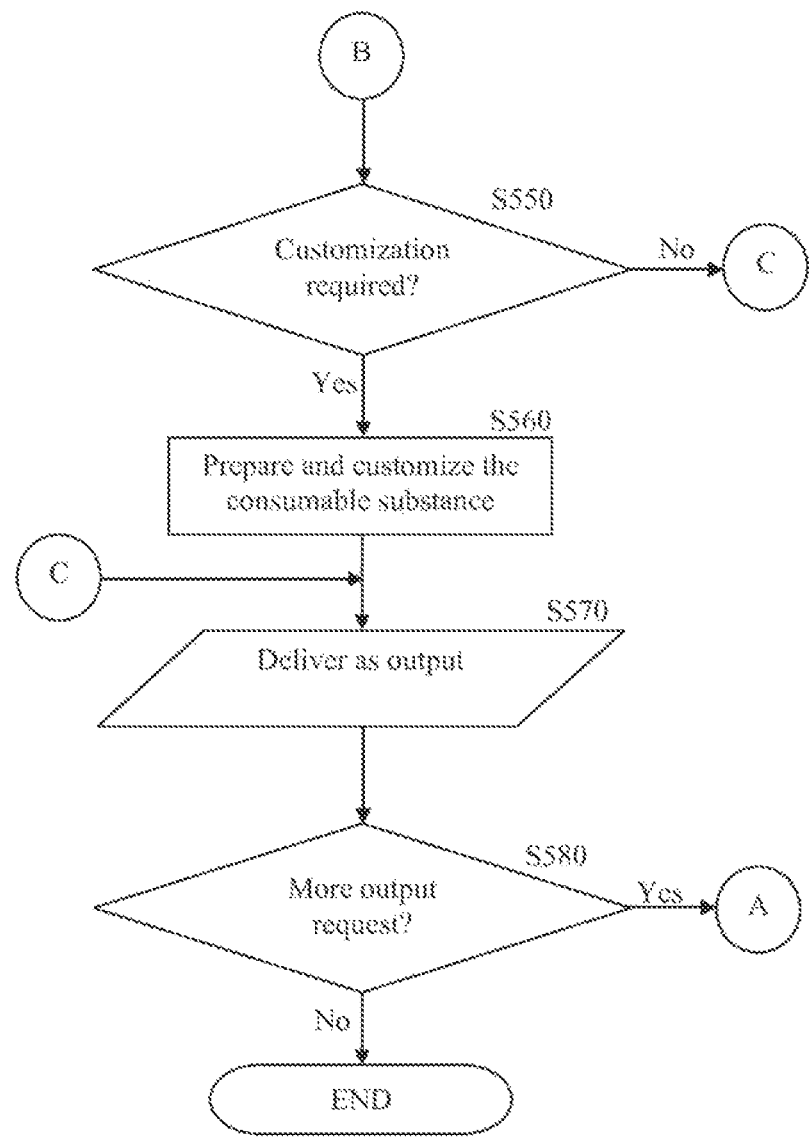

FIG. 5 shows an exemplary and non-limiting flowchart 500 describing the operation of delivering an output of a product substance according to an embodiment. In S510 an output is requested via the control unit 115. In S520, a portion of the upheld culture is flowed to the MU 210 from the BU 135. In S530 it is checked by the control unit 115 whether a modification of the culture is required, and if so execution continues with S540; otherwise, execution continues with S550.

In S540 the culture is modified as a product substance by the MU 210, such as foodstuff or an efficient cosmetic substance to meet expected preferences. In S550 it is checked whether a customization of the upheld culture is required; and if so execution continues with S560; otherwise, execution continues with S570. A request for customization may be received from a user by the interface of the control unit 115. In S560 the culture is customized in the CU 220 according to the user preferences transmitted via the control unit 115. The operation of the CU 220 is discussed above. In S570, the output product substance is delivered through the one or more nozzles 145. In S580 it is checked whether an additional output request is received from a user by the control unit 115, and if so execution returns to S510; otherwise execution terminates.

A person of ordinary skill in the art should readily appreciate that the operation of growing the aquatic organism as described in FIG. 4 and the operation of delivering an output of a consumable substance as described in FIG. 5 may be integrated without departing from the scope of the disclosed embodiments.

The controller unit and the monitoring and controlling processes disclosed herein can be implemented as hardware, firmware, software or any combination thereof. Moreover, the software is preferably implemented as an application program tangibly embodied on a program storage unit or computer readable medium. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such computer or processor is explicitly shown. In addition, various other peripheral units may be connected to the computer platform such as an additional data storage unit and a printing unit.

All examples and conditional language recited herein are intended for pedagogical purposes to aid the reader in understanding the embodiments and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. An apparatus for continuous growth, production and delivery of a product substance, comprising:
   a user interface configured to receive a user request for a product substance;
   at least one input unit for receiving at least one starting material, wherein the starting material is one of at least an aquatic organism;
   at least one growing unit for continuous aquatic growth of the at least one starting material to produce at least a culture;
   at least one buffering unit for accumulating and upholding at least a fraction of the culture grown in the at least one growing unit;
   at least one nozzle for delivery of a demanded fraction of the upheld portion of the culture as the product substance; and
   a controller connected to the at least one input unit, the at least one growing unit, and the at least one buffering unit, wherein the controller is configured to:
      control the operation of the apparatus to ensure that the grown culture and the delivered product substance produced from the grown culture meet predefined requirements,
      control growing conditions within the apparatus, and
      adjust the growing conditions based on a determined demand of the product substance produced by the apparatus, wherein the determined demand is based on the user request received at the user interface, and wherein adjusting the growing conditions comprises at least one of: adjusting the growing conditions within the growing unit to decrease a growth rate of the culture, adjusting the growing conditions within the growing unit to increase the growth rate of the culture, and adjusting growing conditions to modify an ingredient content of the culture.

2. The apparatus of claim 1, further comprises:
at least one first valve connected between the at least one input unit and the at least one growing unit for transferring, wherein the starting material is transferred through the at least one first valve;
a second valve connected between the at least one growing unit and the at least one buffering unit, wherein the at least the culture is transferred through the at least one second valve; and
a third valve connected between the at least one buffering unit and the at least one nozzle, wherein at least a portion of the culture is transferred through the third valve.

3. The apparatus of claim 2, wherein each of the first valve, second valve and third valve is any one of: a unidirectional valve and a bidirectional valve.

4. The apparatus of claim 1, wherein the product substance is at least one of: a foodstuff and a cosmetic substance.

5. The apparatus of claim 1, wherein the at least one starting material is any one of: an edible aquatic organism and an inedible aquatic organism, and wherein the edible aquatic organism includes any one of: a plant from the Lemnaceae family (Duckweed), edible micro algae, and edible macro-algae.

6. The apparatus of claim 5, wherein the plant from the Lemnaceae family (Duckweed) is any one of: *Spirodela, Landoltia, Lemna, Wolffiella*, and *Wolffia* genera.

7. The apparatus of claim 1, wherein the least one starting material is input in a form including at least one of: a pre-matured, juvenile organism, a mature organism, an attenuated form, a dormant form, an etiolated form, and a seed.

8. The apparatus of claim 1, wherein the controller is configured to perform a plurality of measurements of at least one of: physiological conditions, chemical conditions, and physical conditions, wherein the plurality of measurements are digitally read and related to an organism viability, growth, health, safety, nutrition, and biomass yield condition.

9. The apparatus of claim 8, wherein the viability, growth, health, safety, nutrition, and biomass yield condition includes at least one of: types of fertilizers, a temperature range and cycle, a vapor pressure and humidity, potential hydrogen (pH), electrical conductivity (EC), carbon dioxide ($CO_2$) concentration in air and solution, oxygen ($O_2$) concentration in air and solution, light, substrate transparency, water, air, culture density, organism morphology, organism mass density and biochemical features, harvest cycle, reseeding cycle, contamination events, and precipitate.

10. The apparatus of claim 1, further comprises:
a customization unit disposed between the buffering unit and the at least one nozzle and configured to physically process the culture under control of the controller to produce the product substance as a customized substance; and
a modification unit disposed between the buffering unit and the at least one nozzle and configured to change one or more growing conditions of the culture under control of the controller to produce the product substance.

11. The apparatus of claim 10, wherein the customization unit delivers the product substance in a form including any one of: a fresh as-is output, a ground fresh raw substance, a squeezed fresh substance, a substance dehydrated to a pre-defined level, a paste concentrated to a pre-defined level, and a substance as a dry powder.

12. The apparatus of claim 10, further comprises:
a fourth valve for controlling of the transfer of the customized substance from the customization unit to the modification unit;
a fifth valve for controlling of the transfer of the customized substance from the modification unit to the customization unit; and
a sixth valve for controlling of the transfer of the customized substance from the customization unit or modification unit to the at least one nozzle.

13. The apparatus of claim 10, wherein the one or more growing conditions is at least one of: types of fertilizers, temperature range and cycle, vapor pressure and humidity, potential hydrogen (pH), electrical conductivity (EC), carbon dioxide ($CO_2$) concentration in air and solution, oxygen ($O_2$) concentration in air and solution, light, water, air, harvest cycle, and culture density.

14. The apparatus of claim 1, wherein the controller further comprises:
an image sensor configured to capture images of the culture; and
a processor for processing the captured images to determine at least a growth rate of the culture.

15. A method for continuously growing, producing and delivering a product substance, comprising:
receiving at least one starting material in at least one input unit, wherein the starting material is one of at least an aquatic organism;
operating at least one growing unit for continuously growing the at least one starting material to produce at least a culture;
operating at least one buffering unit for accumulating and upholding at least a portion of the culture grown in the at least one growing unit;
receiving a user request for a product substance at a user interface;
operating one or more nozzles for delivering at least a demanded fraction of the upheld culture as the product substance; and operating a controller connected to the at least one input unit, the at least one growing unit, and the at least one buffering unit, wherein the controller is configured to:

ensure that the grown culture meets optimal environmental growth conditions, and the delivered product substance produced from the grown culture meets predefined requirements, control growing conditions of the culture, and adjust the growing conditions based on a determined demand of the product substance produced by the apparatus, wherein the determined demand is based on the user request received at the user interface, and wherein adjusting the growing conditions comprises at least one of: adjusting the growing conditions within the growing unit to decrease a growth rate of the culture, adjusting the growing conditions within the growing unit to increase the growth rate of the culture, and adjusting growing conditions to modify an ingredient content of the culture.

16. The method of claim 15, further comprising:
operating at least one first valve connected between the at least one input unit and the at least one growing unit for transferring, wherein the starting material is transferred through the at least one first valve;
operating a second valve connected between the at least one growing unit and the at least one buffering unit, wherein the at least the culture is transferred through the at least one first valve; and
operating a third valve connected between the at least one buffering unit and the at least one nozzle, wherein the at least the portion of the culture is transferred through the third valve.

17. The method of claim 16, wherein each of the first valve, second valve and third valve is any one of: a unidirectional valve and a bidirectional valve.

18. The method of claim 15, wherein the product substance is at least one of: a foodstuff and a cosmetic substance.

19. The method of claim 15, wherein the at least one starting material is any one of: an edible aquatic organism and an inedible aquatic organism, and wherein the edible aquatic organism includes at least one of: a plant from the Lemnaceae family (Duckweed), edible micro algae, and edible macro-algae.

20. The method of claim 19, wherein the plant from the Lemnaceae family (Duckweed) is any of: *Spirodela, Landoltia, Lemna, Wolffiella* and *Wolffia* genera.

21. The method of claim 15, wherein the at least one starting material is in a form including at least one of: a pre-matured organism, a juvenile organism, a mature organism, an attenuated form, a dormant form, an etiolated form, and a seed.

22. The method of claim 15, wherein the controller further comprises:
performing a measurement of at least one of: physiological conditions, chemical conditions, and physical conditions, wherein the plurality of measurements are digitally read and related to an organism's viability, growth, health, safety, nutrition, and biomass yield condition.

23. The method of claim 22, wherein the viability, growth, health, safety, nutrition, and biomass yield condition includes at least one of: fertilizers, temperature range and cycle, vapor pressure and humidity, potential hydrogen (pH), electrical conductivity (EC), carbon dioxide ($CO_2$) concentration in air and solution, oxygen ($O_2$) concentration in air and solution, light, substrate transparency, water, air, culture density, organism morphology, organism mass density and biochemical features, harvest cycle, reseeding cycle, contamination events, and precipitate.

24. The method of claim 15, further comprising:
operating a customization unit for physical processing of the culture under control of the controller to produce a customized substance, wherein the customization unit is disposed between the buffering unit and the one or more nozzles; and
operating a modification unit for changing one or more growing conditions of the culture under control of the controller to produce the product substance, wherein the modification unit is disposed between the buffering unit and the one or more nozzles.

25. The method of claim 24, further comprising:
delivering the product substance in a form including any one of: a fresh as-is output, a ground fresh raw substance, a squeezed fresh substance, a substance dehydrated to a pre-defined level, a paste concentrated to a pre-defined level, and a substance as a dry powder.

26. The method of claim 24, further comprising:
operating a fourth valve for controlling of the transfer of the customized substance from the customization unit to the modification unit;
operating a fifth valve for controlling of the transfer of the customized substance from the modification unit to the customization unit; and
operating a sixth valve for controlling of the transfer of the customized substance from the customization unit or modification unit to the at least one nozzle.

27. The method of claim 26, wherein the one or more growing conditions is at least one of: types of fertilizers, temperature range and cycle, vapor pressure and humidity, potential hydrogen (pH), electrical conductivity (EC), carbon dioxide ($CO_2$) concentration in air and solution, oxygen concentration ($O_2$) in air and solution, light, water, air, harvest cycle, and culture density.

\* \* \* \* \*